(12) United States Patent
Belli et al.

(10) Patent No.: US 11,226,501 B2
(45) Date of Patent: Jan. 18, 2022

(54) GLASSES COMPRISING BIOSENSORS

(71) Applicant: SAFILO SOCIETÀ AZIONARIA FABBRICA ITALIANA LAVORAZIONE OCCHIALI S.P.A., Padua (IT)

(72) Inventors: Nicola Belli, Padua (IT); Alessandro Sanfelici, Padua (IT)

(73) Assignee: SAFILO SOCIETÀ AZIONARIA FABBRICA ITALIANA LAVORAZIONE OCCHIALI S.P.A., Padua (IT)

( * ) Notice: Subject to any disclaimer, the term of this patent is extended or adjusted under 35 U.S.C. 154(b) by 363 days.

(21) Appl. No.: 16/468,546

(22) PCT Filed: Dec. 1, 2017

(86) PCT No.: PCT/IB2017/057564
§ 371 (c)(1),
(2) Date: Jun. 11, 2019

(87) PCT Pub. No.: WO2018/109606
PCT Pub. Date: Jun. 21, 2018

(65) Prior Publication Data
US 2020/0012126 A1    Jan. 9, 2020

(30) Foreign Application Priority Data

Dec. 13, 2016  (IT) .................. 102016000125574

(51) Int. Cl.
*G02C 1/00*     (2006.01)
*G02C 11/00*    (2006.01)
(Continued)

(52) U.S. Cl.
CPC ............ *G02C 11/10* (2013.01); *A61B 5/0245* (2013.01); *A61B 5/02438* (2013.01);
(Continued)

(58) Field of Classification Search
CPC .......... G02C 11/10; G02C 1/00; G02C 11/04; G02C 11/06; G02C 7/081; G02C 5/14; G02C 5/22; G02C 7/01
(Continued)

(56) References Cited

U.S. PATENT DOCUMENTS 6,176,576 B1    1/2001  Green et al.
9,285,609 B1    3/2016  Rost
(Continued)

FOREIGN PATENT DOCUMENTS

WO    2016052136 A1    4/2016
WO    2016194853 A1    12/2016

*Primary Examiner* — Hung X Dang
(74) *Attorney, Agent, or Firm* — Volpe Koenig (57) ABSTRACT

Glasses that are provided with biosensors for detecting signals and are in contact with the user's head are described, which glasses comprise a front frame (2) for supporting respective lenses (4), a pair of sides (6) articulated to the frame on laterally opposing sides, and a nasal-bearing device (8), each of the sides (6) extending in a longitudinal extension direction and comprising a side body (6*a*) extending into an end side portion (6*b*) in which a particular sensor (25) that makes contact with the head is integrated, and in which the end side portion (6*b*) comprises a pair of branches (26*a*, 26*b*), which extend from a common end (27), which is connected to the side body (6*a*), in the longitudinal extension direction of the side (6) in a manner spaced apart from one another, one (26*a*) of the branches being provided with an internal cavity (29) for housing a core (30) made of a conductive metal material and both the branches (26*a*, 26*b*) being made of a resiliently pliable and electrically conductive material.

9 Claims, 12 Drawing Sheets

(51) Int. Cl.
*A61B 5/024* (2006.01)
*A61B 5/0245* (2006.01)
*A61B 5/00* (2006.01)
*B29D 12/02* (2006.01)
*G02C 5/00* (2006.01)
*G02C 5/16* (2006.01)
*A61B 5/369* (2021.01)

(52) U.S. Cl.
CPC ............ *A61B 5/6803* (2013.01); *B29D 12/02* (2013.01); *G02C 5/008* (2013.01); *G02C 5/16* (2013.01); *A61B 5/369* (2021.01); *G02C 2200/16* (2013.01)

(58) Field of Classification Search
USPC ............... 351/158, 41, 111, 121, 49; 349/13
See application file for complete search history.

(56) References Cited

U.S. PATENT DOCUMENTS

| | | | |
|---|---|---|---|
| 2009/0105605 A1 | 4/2009 | Abreu | |
| 2014/0232981 A1* | 8/2014 | Sugihara | ............ G02B 27/0176 351/158 |
| 2015/0049295 A1* | 2/2015 | Larson | ................... G02C 5/18 351/117 |
| 2018/0049664 A1 | 2/2018 | Miyazaki | |

* cited by examiner

GLASSES COMPRISING BIOSENSORS

TECHNICAL FIELD

The present invention relates to glasses comprising biosensors having the characteristics stated in the preamble of the main claim, claim 1.

TECHNOLOGICAL BACKGROUND

The invention falls within the specific technical field of glasses that comprise biosensors integrated in the front frame and/or on the lateral sides thereof; the term "biosensor" meaning a sensor for detecting electrical signals relating to vital functions, for example brain functions, by means of the localised sensor contact in particular zones of the surface of the head.

The use of sensors of this type on the frames of glasses is becoming widespread, in particular due to the potential advantageous applications that may derive from diagnosing the vital functions in general, in particular brain functions. In fact, sensors of this type make it possible, for example, to detect changes in brainwaves (electroencephalography), the position of the eyes (electrooculography), contractions of the muscles around the eyes (electromyography), and heart functions (electrocardiography).

The knowledge of the state of these functions that can be easily detected by means of the sensors, which are suitably integrated in the frame, as a result of the localised contact between said sensors and the user's head, advantageously makes it possible to take action to control and monitor the mental-physical states of the person, in order if necessary to be able to correct or advise of situations that put the person's health and safety at risk. Take the monitoring of states of stress, and more generally of fatigue, for instance, which may occur when carrying out work, sports and recreational activities.

DESCRIPTION OF THE INVENTION

In this context, the main object of the invention is to provide glasses provided with biosensors, the structure and function of which are designed to improve the technical solutions known in the prior art, in particular those associated with the problems relating to the integration of the sensors in the frame components, in order to make it easier to produce and to assemble the sensors on the glasses, while ensuring sufficient reliability and efficiency thereof and reasonable comfort when wearing the glasses on the head, in particular where the sensor makes localised contact with the head.

This object and other objects that will become clear in the following are achieved by the invention by means of glasses that comprise biosensors, which are produced in accordance with the appended claims.

BRIEF DESCRIPTION OF THE DRAWINGS

The features and advantages of the invention will become clearer from the following detailed description of a number of preferred embodiments thereof, which are shown by way of non-restrictive example with reference to the appended drawings, in which:

FIG. 14A is a plan view of the lateral side in FIG. 13, FIGS. 15 and 16 are sectional views according to the lines XV-XV and XVI-XVI in FIG. 14, respectively.

PREFERRED EMBODIMENTS OF THE INVENTION

With reference to the above-mentioned figures, reference numeral 1 indicates glasses as a whole, which comprise biosensors and are formed in accordance with the present invention.

The glasses comprise a front frame 2 having a pair of respective rims 3 for supporting corresponding lenses 4, which are connected to one another in the centre by a bridge 5 that extends in the nasal region. Reference numeral 6 indicates both the lateral sides of the glasses, which are hinged with respective end pieces 7 provided on laterally opposing sides of the frame 2. The glasses are provided with biosensors located in the central region of the frame that rests against the nose and in the rear zone of the ears, where the lateral sides rest against the user's head. In this context, the term "biosensor" is understood to mean any sensor designed to detect electrical signals relating to vital functions of the person, for example brainwaves, heartbeat or other vital parameters.

As will become clear in the following, the sensors are therefore designed to function as electrodes that come into contact with the skin in order to detect the electrical signal and transfer it, by means of a system of electrical-signal conductors provided in the frame, to an electronic module provided with a circuit unit for managing the signals detected.

The glasses are provided with a nasal-bearing device 8, which comprises a framework 9 that is structurally independent of the front frame 2 and can be detachably coupled to said frame.

A first and a second nasal-bearing element 10, 11 are provided on the framework 9 so as to be opposite one another, in each of which elements a first 10a and a second 11a nasal sensor is integrated, which can make surface contact with corresponding laterally opposite zones of the nose.

A third sensor, indicated by reference numeral 12, is provided in the centre of the framework 9, above the sensors 10a, 11a and at a spacing therefrom, so as to enter into superficial contact with the face at the bridge of the nose, just below the "glabella" of the head, when the glasses are being worn.

The sensors 10a, 11a and 12 are advantageously made of a resiliently pliable material that is electrically conductive, for example an electrically conductive elastomer or rubber, so as to ensure comfort and fit adaptability with regards to the bearing contact on the one hand, and for the sensors to fulfil the electrode function in order to detect the respective signals on the other hand. In more detail, the framework 9 comprises a pair of opposite arms 13, which extend with equal orientation from and are interconnected by a central plate-shaped crosspiece 14, which is provided with a through-hole 15 in order to tightly fasten the framework 9 to the inside of the front frame 2 using a screw 16, i.e. the side facing the user's face when the glasses are being worn. In an alternative variant, the screw 16 for fixing the framework 9 to the front frame 2 can be provided in a different position, for example in the lower part of the frame, such that the longitudinal axis of the screw 16 is parallel to the centre line X in FIG. 7. In this case, the longitudinal axis of the hole 15 made in the framework 9 for the screw 16 to pass through is also parallel to the axis X; the corresponding hole for fixing the screw 16, which hole is made in the bridge 5, also being parallel to the axis X. In this configuration, the respective geometry and thicknesses of the bridge 5 and of the framework 9 in the respective lower parts have to be appropriately modified with respect to those illustrated with regard to the preferred embodiment, so as to obtain a volume of material that is sufficiently extensive in the framework and the bridge, so as to allow the screw to be inserted and gripped.

Figure 7:
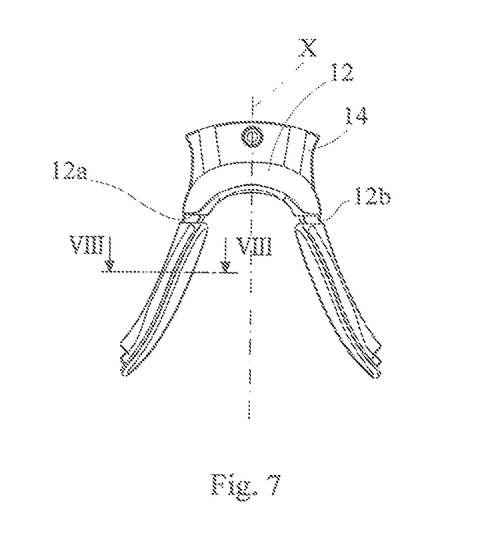
FIG. 7 is a front elevation of the detail in FIG. 5.
Figure 8:
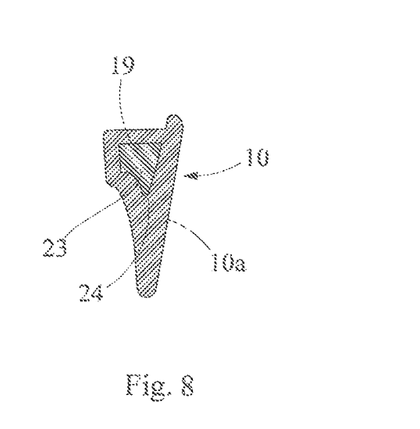
FIG. 8 is a sectional, enlarged view according to the line VIII-VIII in FIG. 7, FIGS. 9 and 10 are perspective views of a component of the detail in FIG. 5, FIGS. 11 and 12 are schematic perspective views relating to steps of producing the detail in FIG. 5, FIGS. 13 and 14 are side elevations of one of the lateral sides of the glasses in FIG. 1.
Figure 9:
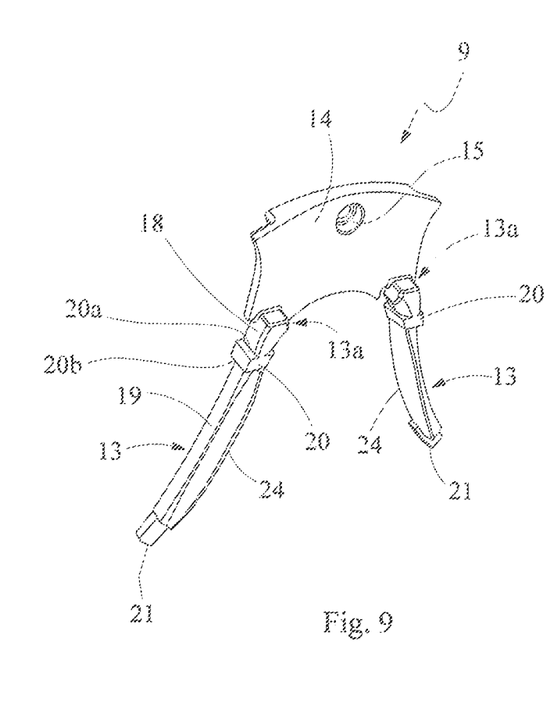
Figure 10:
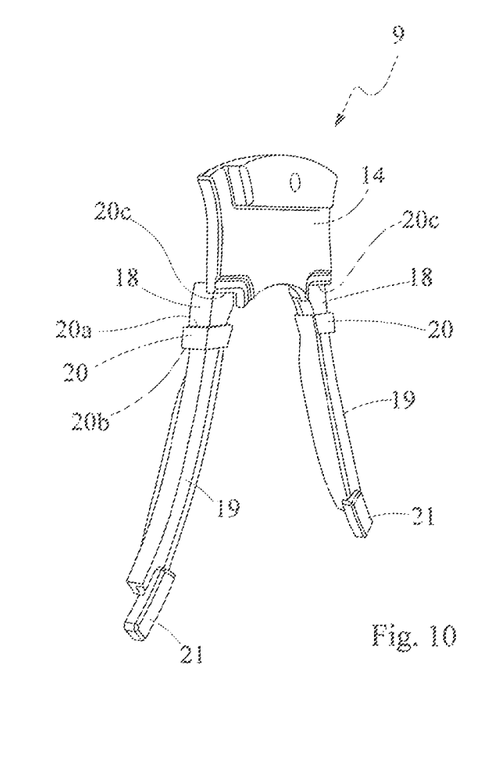

The arms 13 have mirror symmetry with respect to a median plane of symmetry, which is indicated by the centre line X in FIG. 7. On account of this symmetry, only one of the arms 13 will be described in detail.

The particular nasal-bearing element 10 (11) is mounted on each arm 13, the sensor 12 (which is suitably also referred to as the "glabella sensor" in the text) extending in the form of a bridge between the arms 13 and remaining at a spacing from the crosspiece 14 (protruding towards the face when the glasses are being worn) in order to ensure that it stays in bearing contact with the zone of the bridge of the nose, said sensor 12 also being integrally connected to the respective arms 13 of the framework at its two opposite ends 12a, 12b.

As is clearly shown in the figures, each nasal-bearing element 10a, 11a, in which the corresponding sensor is integrated, is shaped as a "small nose plate" so as to comfortably rest against the sides of the nose, the glabella sensor 12 in turn being "saddle" shaped in order to ensure effective and comfortable contact on the bridge of the nose.

A first and a second arm portion, indicated by reference numerals 18, 19, respectively, are located on each arm 13 starting from the end 13a thereof that connects to the crosspiece 14, between which portions an arm section 20 is interposed, which is larger than the portions 18, 19 (the size being considered in the direction transverse to the longitudinal extension direction of said portions). Said section 20 defines on the portions 18, 19 respective surface shoulders 20a, 20b, against which there can stop respectively the corresponding end 12a (12b) of the glabella sensor 12, which end is coupled to the portion 18, and the corresponding nasal sensor 10a (11a) that is coupled to the region 19.

Each end 12a, 12b of the sensor 12 is held on the corresponding portion 18 between the shoulder 20a and an opposite bearing surface 20c provided by the crosspiece at the upper end 13a of the arm.

A particular limb 21, which can be received and held in a seat 22 provided in the corresponding rim 3 of the frame, is provided in the second region 19, near to the free end of the arm 13.

In a preferred embodiment, the framework 9, the nasal-bearing elements 10, 11, which form the respective sensors 10a, 11a, and the sensor 12 are formed by means of injection-moulding plastics material and, more particularly, all the sensors are over-moulded on the framework.

The production process advantageously provides a first step in which the framework is formed by means of injection-moulding a rigid plastics material, the framework having a moderate degree of elastic deformation due to its structure. In a subsequent second step, the sensors 10a, 11a and 12 are directly over-injected on the framework 9 in the corresponding positions in electrically conductive elastomeric material or in conductive rubber.

In one variant, the sensors 10a, 11a and 12 can be formed separately from one another and from the framework 9, again by means of injection-moulding. The sensors are formed having attachment portions having cavities in the form of through-openings 23, in which the corresponding portions 18, 19 of the arms of the framework engage with a substantial positive fit.

In this case, the method provides a first step, as described above, in which the framework 9 is formed by means of injection-moulding using a rigid plastics material, the framework having a moderate degree of resilient deformation on account of its structure.

Figure 11:
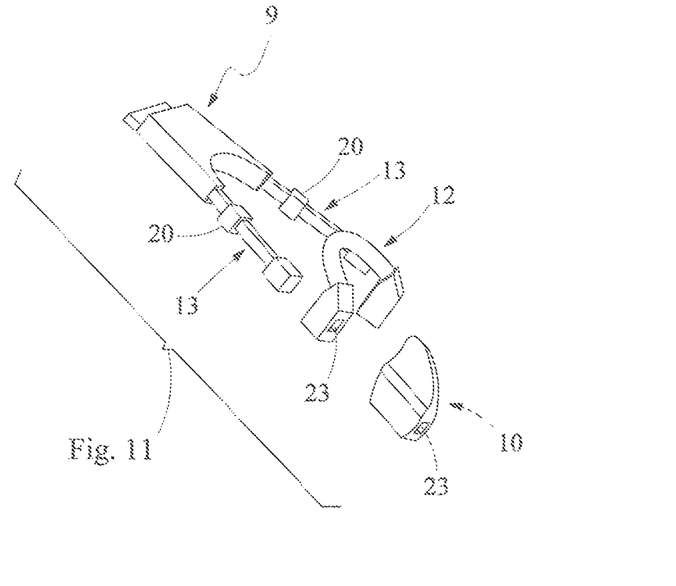
Figure 12:
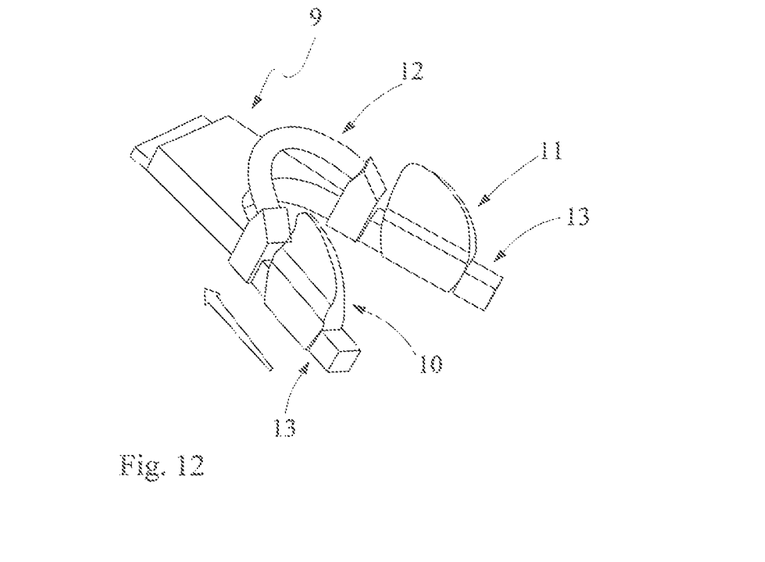
Figure 13:
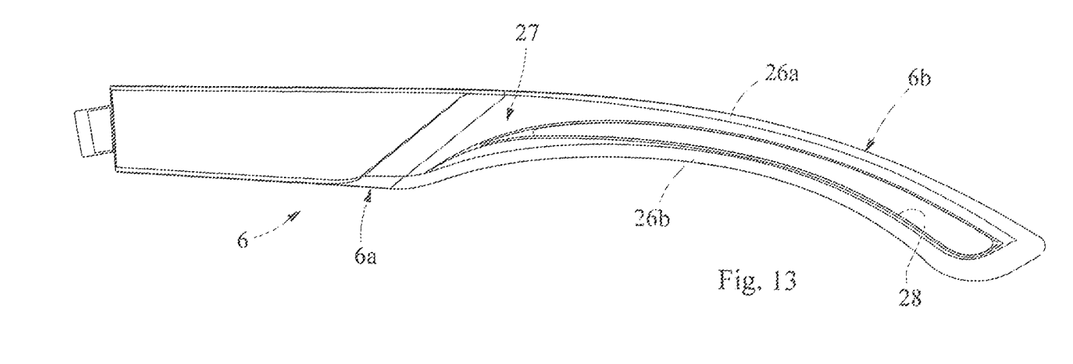

Said first step is followed by a second step in which the sensors are injection-moulded, separately from the framework, using an electrically conductive elastomer. In a subsequent step, the sensors are then mounted on the corresponding arms of the framework, and are fitted by means of a relative sliding movement, the regions of the arms engaging in the attachment openings 23 until they reach the corresponding coupling positions. FIGS. 11 and 12 schematically show the method steps described above, in which the sensors are coupled to the framework.

In this context, it may be advantageous to use a thermoplastic elastomer selected from those currently available in the plastics materials sector, including the material known as "Pre-Elec® TPE 1502", for example, which is produced by the Finnish company PREMIX, is based on a thermoplastic polymer and is made electrically conductive by the use of suitable additives, such as carbon black.

In fact, at the same time "Pre-Elec® TPE 1502" has values suitable for all the technological properties that are basically required for implementing the invention. These properties include: high electrical conductivity, a tendentially low modulus of elasticity and surface hardness, a good degree of softness and resilient compliance.

It is understood that the material cited above is just one example of an elastomer that can be used for implementing the invention proposed here, and that the present invention can also be implemented by using other alternative materials that are available in the plastics materials sector and that have technical features which are equivalent to those of PreElec® TPE 1502".

In another variant, the sensors can be formed by means of casting.

Reference numeral 24 denotes on each portion 19 of the corresponding arm a protrusion which protrudes from the profile of said portion and acts as an anti-rotation element for the respective nasal sensor mounted on said region. Once the sensors have been formed and assembled on the framework 9, said framework is connected to the front frame 2.

Figure 4:
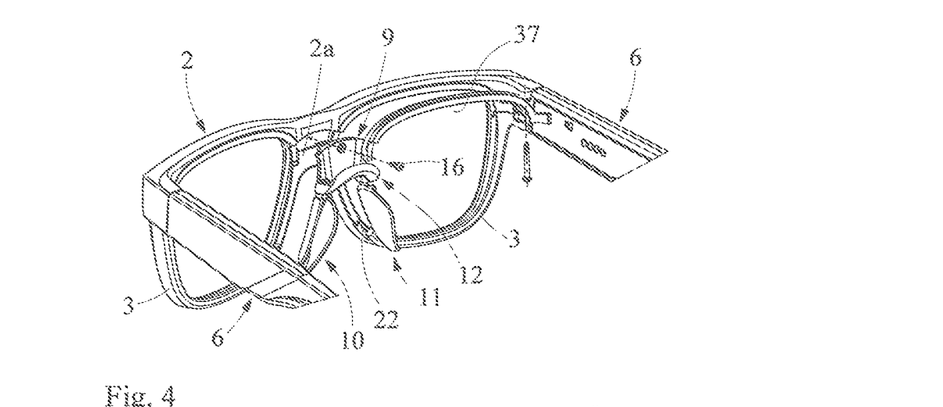
FIG. 4 is a perspective partially sectional and partially removed view of the glasses in the preceding figures.
Figure 5:
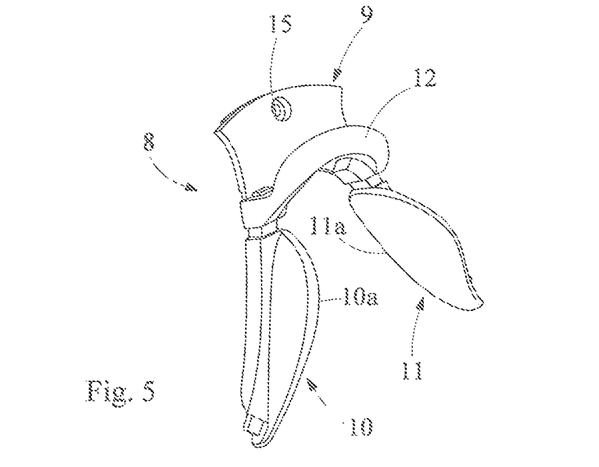
FIGS. 5 and 6 are perspective enlarged views of a detail of the glasses in the preceding figures.
Figure 6:
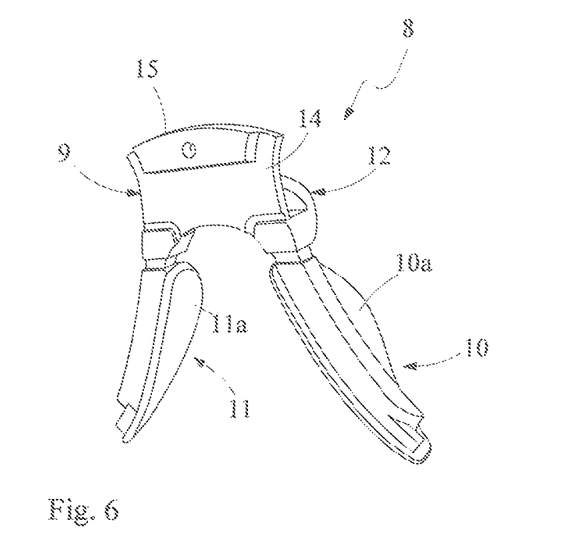

A recess 2a is provided in the frame at the bridge 5 and along part of the rim portions 3 that extend below the bridge. Said recess 2a is formed as a depression in the surface of the corresponding frame zone and is shaped so as to receive the framework 9 together with the arms thereof, as shown in FIG. 4. Said framework is fixed by means of the fastening screw 16 engaging in the frame, passing through the hole 15, and the limbs 21 at the ends of the arms of the framework are also received and held in the seats 22 of the frame.

In the fixing sequence, the limbs 21 are inserted into the respective seats 22 in advance. In this regard, the framework 9 is formed so as to have, in the lower part of the arms 19, a nominal width (distance between the opposite limbs 21) that is greater than the mounting width, i.e. the effective width measured once the framework has been assembled on the frame. In this way, the framework is resiliently "preloaded" (by compressing the arms moving towards one another), and, once applied to the framework, it tends to move the two ends, which are lower than the respective portions of the rims of the frame, towards one another due to the resilient return, thus ensuring that the limbs 21 are coupled and held in the respective seats 22.

Once the limbs 21 have been inserted into the seats 22, the framework is then connected to the frame by applying the fastening screw 16.

With regard to the materials that can be used to produce the framework 9, various types of plastics materials are suitable. By way of non-limiting example, polyamide-based plastics materials can be cited (including the material commercially known as "Grilamid® TR 90"), or polypropylene-based plastics materials.

In addition, with regard to the production of the front and the sides (described below in the text), use can advantageously be made of various types of plastics materials, including the materials cited that may be used for producing the framework 9.

Since the sensors need to be particularly sensitive to the signal in order to detect some specific types of "biosignals" or electrical signals relating to vital functions, it is possible that the degree of electrical conductivity characteristic of the conductive elastomer is not sufficiently high to guarantee that the biosensor made of said elastomer functions properly. The problem arises, for example, when detecting biosignals characterised by a particularly low intensity, particularly when compared with the typical intensity of other concomitant biosignals, i.e. biosignals that are present on the surface of the user's head at the same time. Although the various biosignals that can be detected on the head or on the face at the same time are distinguished by different oscillation frequencies, they tend to overlap, thus sometimes determining a type of background "noise", which cannot be distinguished in detail.

A piece of software integrated in the electronic module is tasked with "distinguishing" the sought-after biosignal, recognising it with respect to the other concomitant signals and interpreting it for subsequent processing. In some cases, however, the software can require a set of data, in the form of detected electrical signals of a particularly high intensity and accuracy, resulting in the need for the extremely effective electrical transmission of the biosignal from the skin to the electrical circuit connected to the electronic module.

Since the efficiency with which electricity is transmitted to the interface with the skin depends on both the degree of electrical conductivity of the elastomer and on the extent of the contact surface between the skin and the elastomeric sensor, when it is not possible to increase the quality of the signal detection by increasing the contact surface between the sensor and the skin, that is by modifying the shape and/or dimensions of said sensor, solutions are used that make it possible to significantly increase the degree of electrical conductivity of the first surface layer of said sensor.

Once the signal that can be detected on the skin of the face or of the head is picked up in a clearer manner due to the greater degree of electrical surface conductivity of the biosensor, said signal can then be transmitted to the electrical circuit on the inside of the frame by means of electrical conduction inside the volume of the component made of a conductive elastomer, said volume being interposed between the outer more conductive layer and the conductor on the inside of the sensor that is delegated to the passage of the signal to the electrical circuit inside the frame.

The preferred solution for the possible increase in the degree of electrical surface conductivity of the biosensor made of a conductive elastomer involves using electrically conductive coatings, for example electrically conductive inks or varnishes.

In order to be easily available in the technical field, such products are available in various alternative formulations or compositions, having various possible modes of application. Depending on requirements, in addition to the type of coating, it is also possible to select whether to cover the entire surface of the biosensor with the electrically conductive coating or whether to apply said coating to just part of the sensor by covering in a targeted manner only those portions of the surface of the biosensor that are in direct contact with the skin and that also require a higher degree of electrical surface conductivity.

In accordance with the invention, sensors of the type described above are also provided on one or both of the lateral sides 6.

Due to the mirror symmetry thereof, only one of the sides will be described in detail.

With particular reference to FIGS. 13 to 16, each side 6 comprises a side body 6a provided for hinging with the front end piece, which extends into an end side portion 6b in which there is integrated a sensor 25 that makes contact with the head in the rear zone of the ear, where the side laterally rests against the head.

The end portion 6b is designed to have a pair of branches 26a, 26b extending from a common end 27 connected to the side body, said branches extending in the longitudinal direction of extension of the side so as to be spaced apart from one another. In a configuration in which a slotted through-opening 28 having a closed contour is defined between the branches, the branches 26*a*, 26*b* are likewise connected to one another at the free end of the end portion 6*b*, which is opposite the end 27.

One of the branches, preferably the upper branch 26*a* (which is at a greater vertical distance from the ear when in contact with the head) is advantageously provided with an inner cavity 29 for housing a core 30 of the side, which is made of an electrically conductive metal material or is coated with electrically conductive metal material.

Merely by way of example, it is advantageous for the core 30 to be made of steel and then coated with a conductive gold layer, which is deposited by means of galvanisation.

The end portion 6*b* (comprising the branches 26*a*, 26*b*) is likewise made of a resiliently pliable material that is electrically conductive, for example of an electrically conductive elastomer or rubber.

The electrically conductive material is sensitive to the electrical potential that can be detected on the skin and the electrical signal or potential is transmitted from the conductive elastomeric material to the metal core, which acts as an electrical conductor.

At the end 27 of the end side portion, the inner core 30 extends into a limb 31 for insertion into the side body 6*a*. By means of said limb 31, the core 30 is likewise electrically connected to a module or electronic circuit 32 (shown schematically in FIG. 24), which is accommodated in a housing 33 provided inside the side body 6*a*.

Figures 14, 14A:
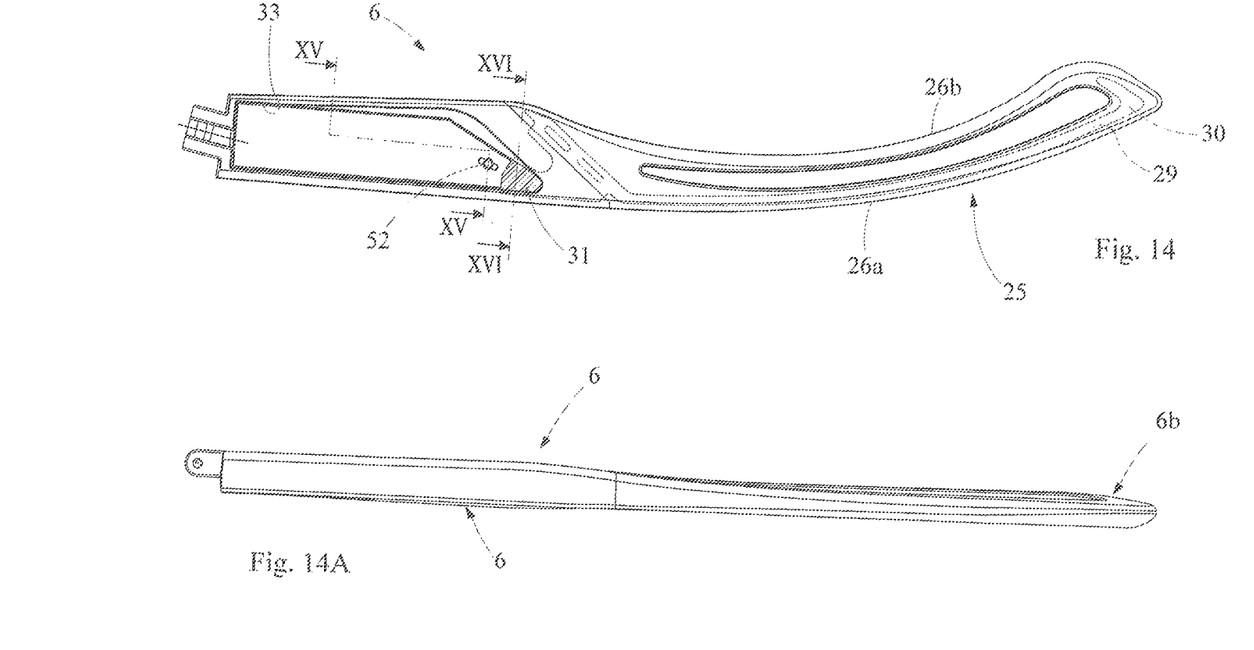
Figure 15:
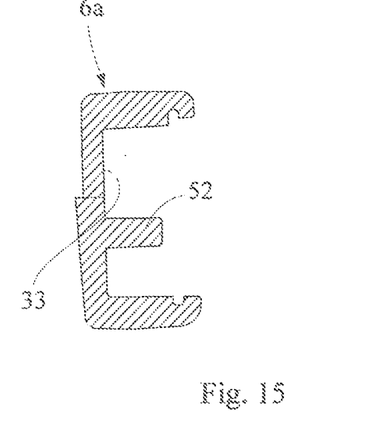
Figure 16:
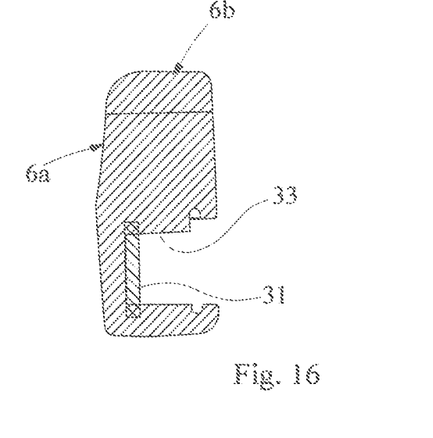
Figure 17:
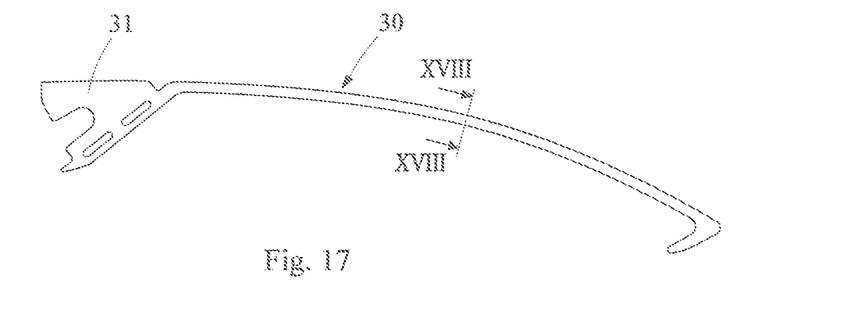
FIG. 17 is a lateral elevation of a detail of the side in FIG. 13.
Figure 18:
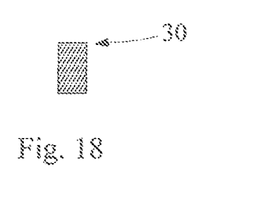
FIG. 18 is a sectional view according to the line XVIII-XVIII in FIG. 17, FIGS. 19 and 20 are partially sectional perspective views of a detail of the inner frame side.

As shown in FIG. 14, the insertion limb 31 extends so as to protrude into the inside of the housing 33 in order to electrically connect it to the electronic module 32.

Said housing 33, which remains defined inside the dimensions of the side, is open on the inner side of the side (the side facing the user's head) and is provided with a closure cover 34 that can be detachably coupled.

In one embodiment, the housing 33 on one of the sides is intended for accommodating the electronic module while the housing formed on the other side is intended for accommodating a battery 45 for supplying electricity to the electronic module and the sensors. The battery 45 is preferably a rechargeable, non-removable battery. Alternatively, it may also be a removable battery. In addition, it may be a non-rechargeable battery, in which case it has to be removable in order to be able to replace it once it is discharged.

If the housing formed on one of the sides is intended for accommodating a battery for supplying electricity, the shape and the dimensions of the core 30 of said side are the same as the shape and dimensions of the core 30 of the other side, the housing of which is intended to accommodate the electronic module. This is also the case in particular for the limb 31 of the core, and is the same for both the cores of the two sides.

In fact, in the case of the side intended to house the battery, the insertion limb 31 of the core 30 also extends so as to protrude into the inside of the housing 33 in order to electrically connect it to a second electronic circuit 46, which is characterised by smaller dimensions and fewer functions than the main circuit or electronic module 32, which is housed in the corresponding side. In fact, the only functions of the second electronic circuit 46 are to detect the electronic signal originating from the sensor used in said side, to transmit this signal to an electrical circuit inside the frame (Flex PCB) (described in detail in the following), and to allow said electrical circuit to be connected to the battery.

Figure 24:
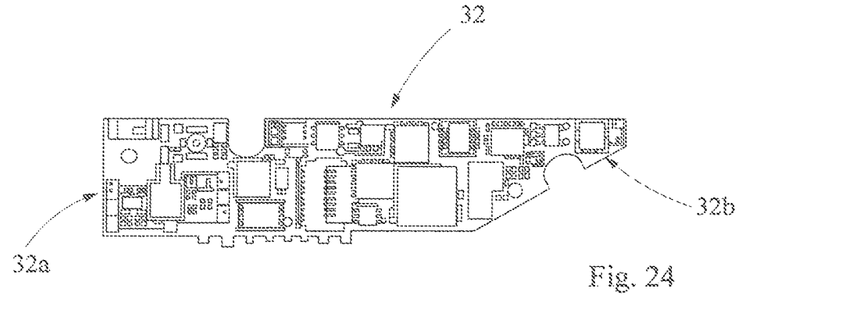
FIG. 24 is an enlarged view of an electronic module intended to be housed in the frame of the glasses in the preceding figures.

In FIG. 24, one end 32*a* facing the hinged side of the side and an opposite end 32*b* facing the side of the end side portion and capable of overlapping and electrically contacting the insertion limb 31 are located in the module or electronic circuit 32.

Figure 25:
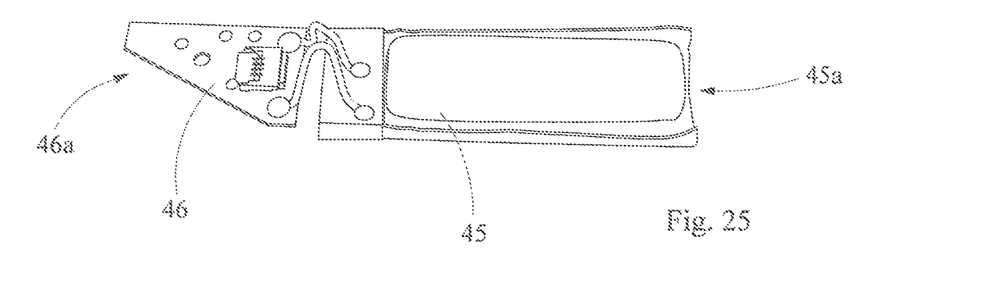
FIG. 25 is an enlarged view of a battery, for supplying power, associated with a printed circuit board, which are intended to be housed in the frame of the glasses in the preceding figures.

In FIG. 25, the battery 45 for supplying electricity is shown coupled (by an electrical connection) to the electronic circuit 46. Reference numeral 46*a* denotes the free end of the circuit facing the side of the end side portion, which is capable of overlapping and electrically contacting the insertion limb 31. Reference numeral 45*a* instead designates the end of the battery 46 (which is longitudinally opposite the end 46*a*) that faces the hinged side of the side.

Other configurations are, however, possible. It may also be provided that one housing or the other housing of the corresponding sides accommodates, in addition to or alternatively to the electronic module or to the battery, other devices or components for managing or transmitting the signals detected by the sensors.

On account of both the features of the preselected metal material and the overall geometry of the core 30, said core is plastically deformable, therefore making the end side portion 6*b* "adjustable", i.e. shapeable, in order to adapt the shape thereof to the user's head for a comfortable and stable fit of the glasses.

In fact, if the side end 6*b* is subjected to an adaptation procedure, the core 30 is plastically deformed and tends to maintain its new shape, while the elastomer (or rubber) that encompasses the core instead tends to resiliently deform due to it being resiliently pliable, thus following the new folded shape of the core, and thus being constrained to the new shape assumed by the rigidity of the core.

Due to the slotted shape of the end portion 6*b*, the lower branch 26*b*, which is spaced apart from the other branch and is not affected by the presence of a metal core, can be resiliently deformed to a greater extent than the upper branch 26*a*. This degree of deformability allows for the best possible adaptation of the bearing on the ear, thus guaranteeing secure and reliable electrical contact as well as adequate overall fit comfort of the glasses.

The end side portion 6*b* is formed using injection-moulding technology, the upper branch 26*a* being over-moulded on the metal core 30 in the moulding step.

A preferred method for producing each side 6 provides that, in a first step, the side body 6*a* is produced by injection-moulding a rigid plastics material, with over-injection on the end of the core 30 that engages with the insertion limb 31. In a subsequent second method step, the end 6*b* made of electrically conductive elastomeric material is over-moulded on the remaining part of the core 30, the branches 26*a*, 26*b* of the side end thus being formed in this step. In order to electrically connect the electronic module (or battery) to the sensors and in order to electrically transmit the signals detected by the sensors, in particular the sensors located in the nasal-bearing device 8, an electric circuit formed as a printed circuit board, also known in the technical field as a "Flex PCB") (Flexible Printed Circuit Board) is used. Each portion of this circuit, where shown in the figures, is designated by reference numeral 35.

Part of the circuit 35 is housed inside the front of the frame 2, which engages with the upper portions of the lens-holder rims 3 extending along the brow-ridge region, and part of said circuit is housed inside the hinged zone between the side and the end piece, until it reaches the inside of the corresponding housing 33 of the side.

In order to house the circuit 35 on the frame, the inner side of said frame is provided with respective seats 36 made in the rims 3 and in the end pieces 7, said seats being coupled to respective closure inserts 37 so as to hide the circuit 35 extending along the frame portion.

It is noted how, once each insert 37 has been applied to the front itself with its side facing the front of the frame, it contributes to forming the inner groove 37a or "small channel" for retaining the lens, over the entire length of said insert, which extends from the edge that adjoins the nasal-bearing device to the edge that adjoins the hinge.

Figure 1:
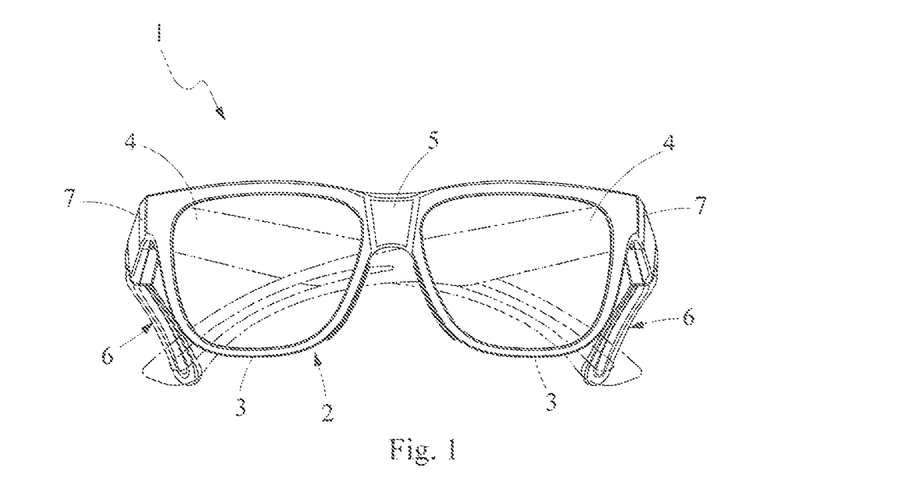
FIG. 1 is a front elevation of glasses according to the present invention.
Figure 1A:
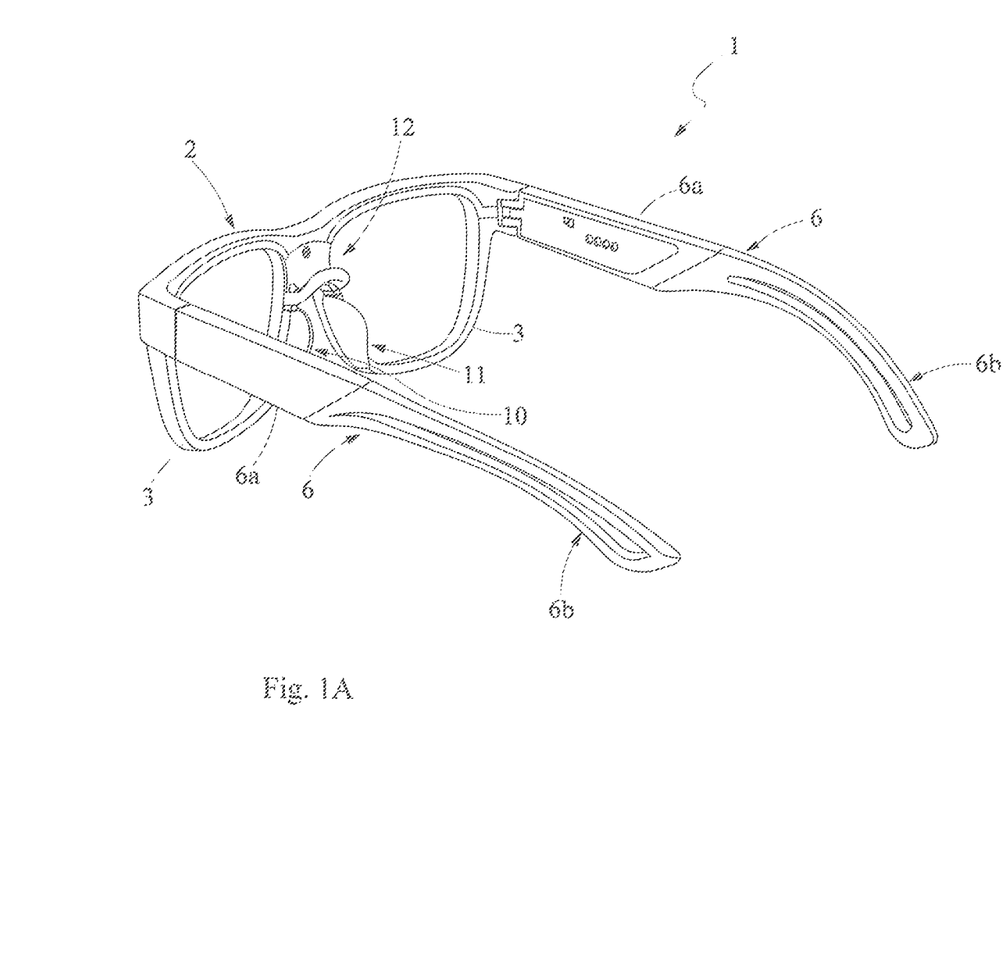
FIG. 1A is a perspective view of the glasses in FIG. 1.
Figure 2:
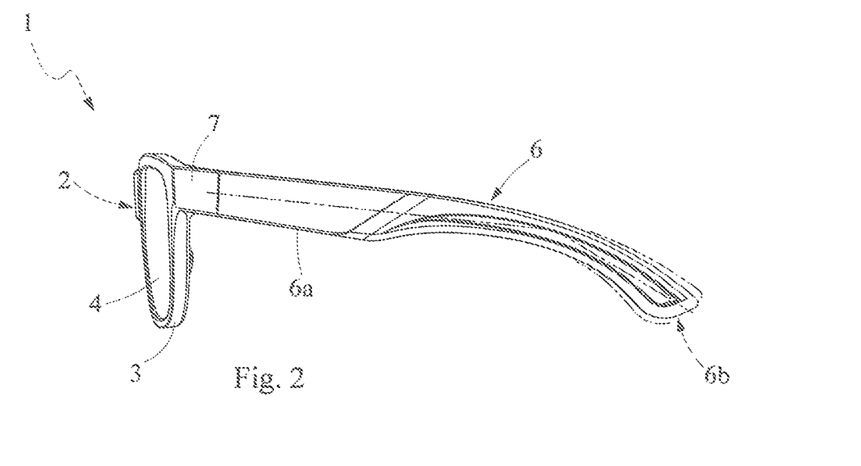
FIGS. 2 and 3 are a side elevation and a plan view, respectively, of the glasses in FIG. 1.
Figure 3:
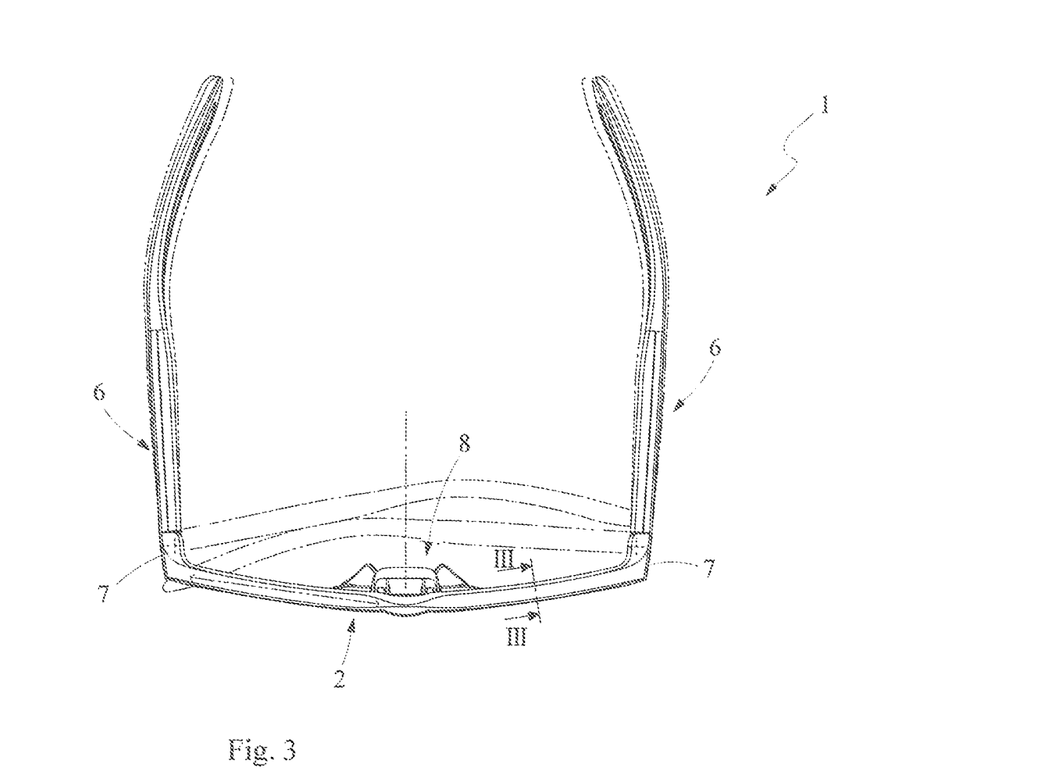
Figure 3A:
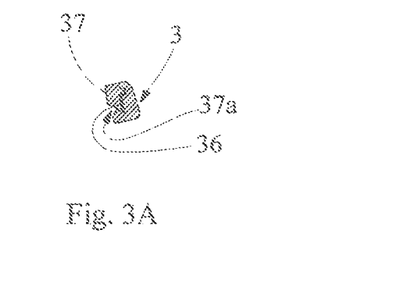
FIG. 3A is a sectional view according to the line in FIG. 3.

The section of the "small channel" for lenses, which is typically characterised by a "U"-shaped profile, and can accommodate and hold the outer edge of the lens inside the front, is visible in FIG. 3A.

Figure 19:
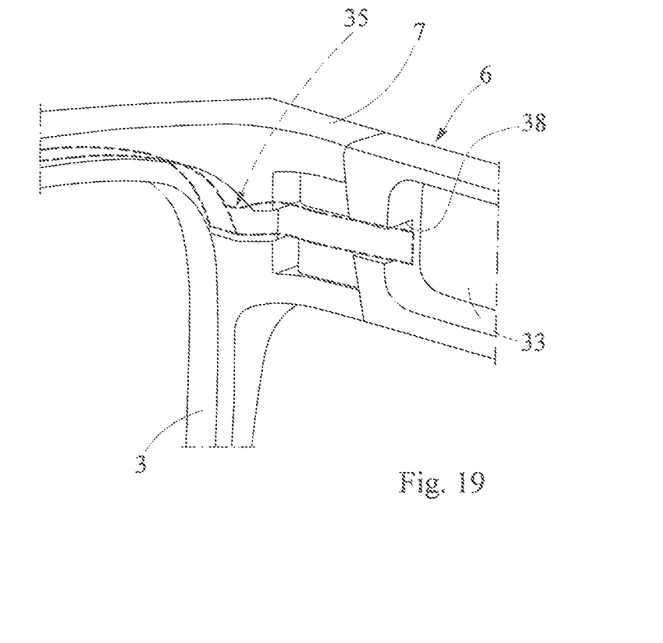
Figure 20:
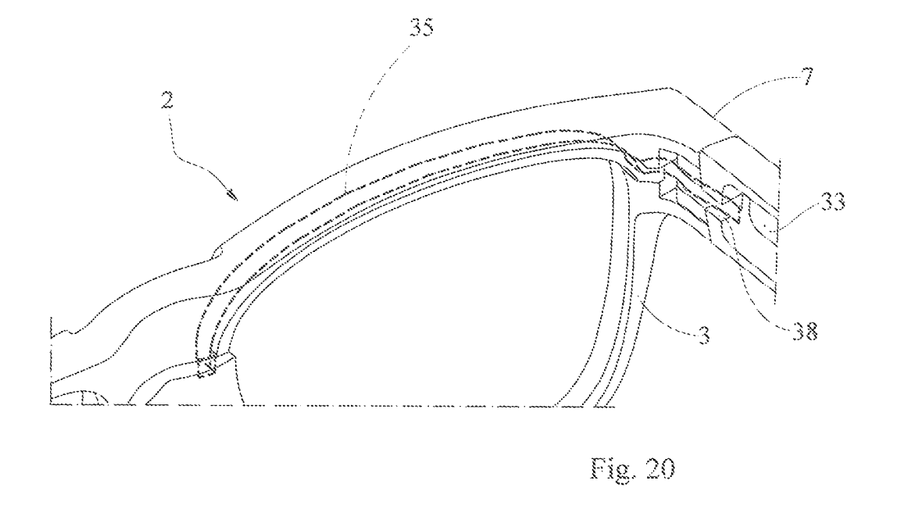
Figure 22:
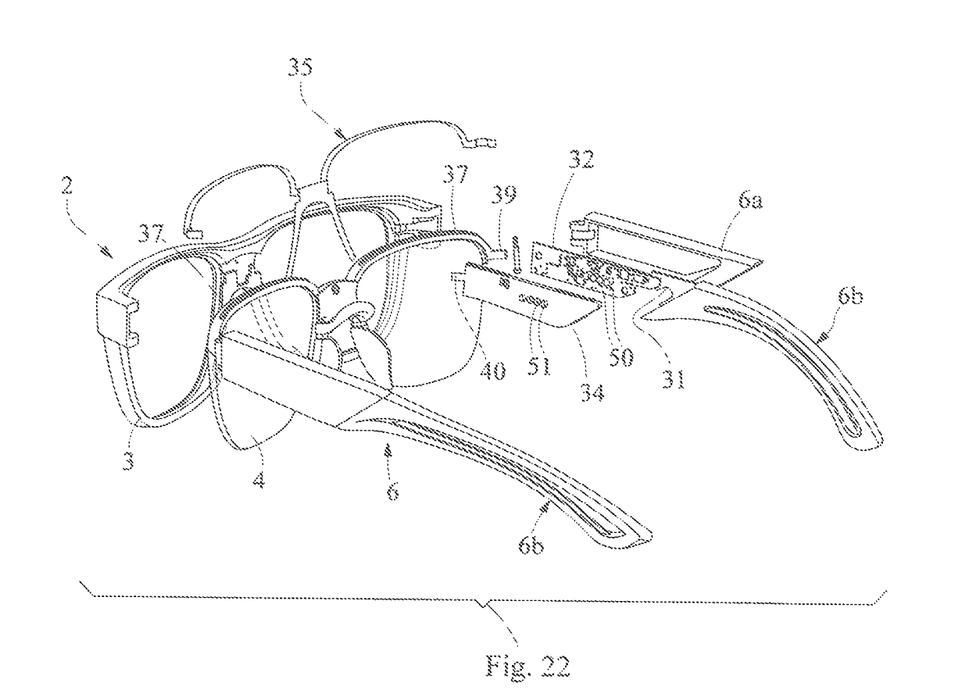
FIG. 22 is an exploded perspective view of the entire glasses in the preceding figures.
Figure 23:
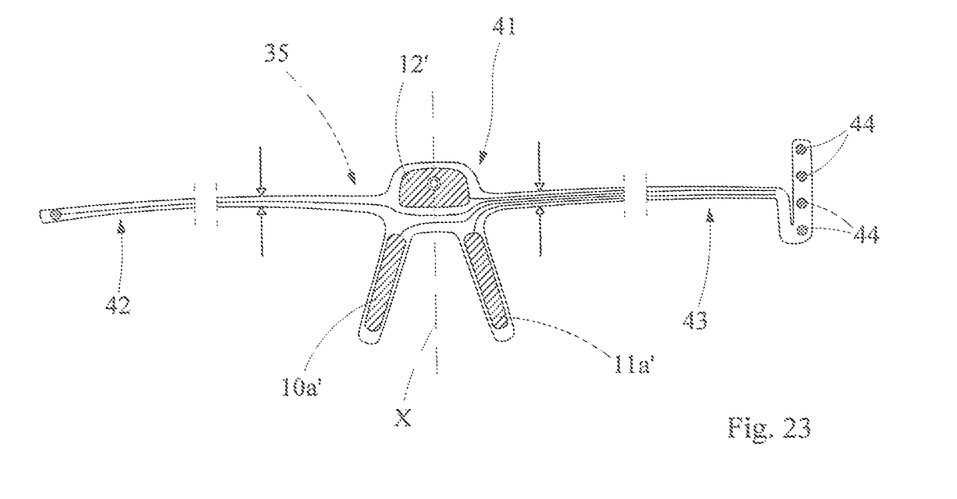
FIG. 23 is a schematic view of an embodiment of a flexible electrical circuit integrated in the glasses in the preceding figures.
Figure 26:
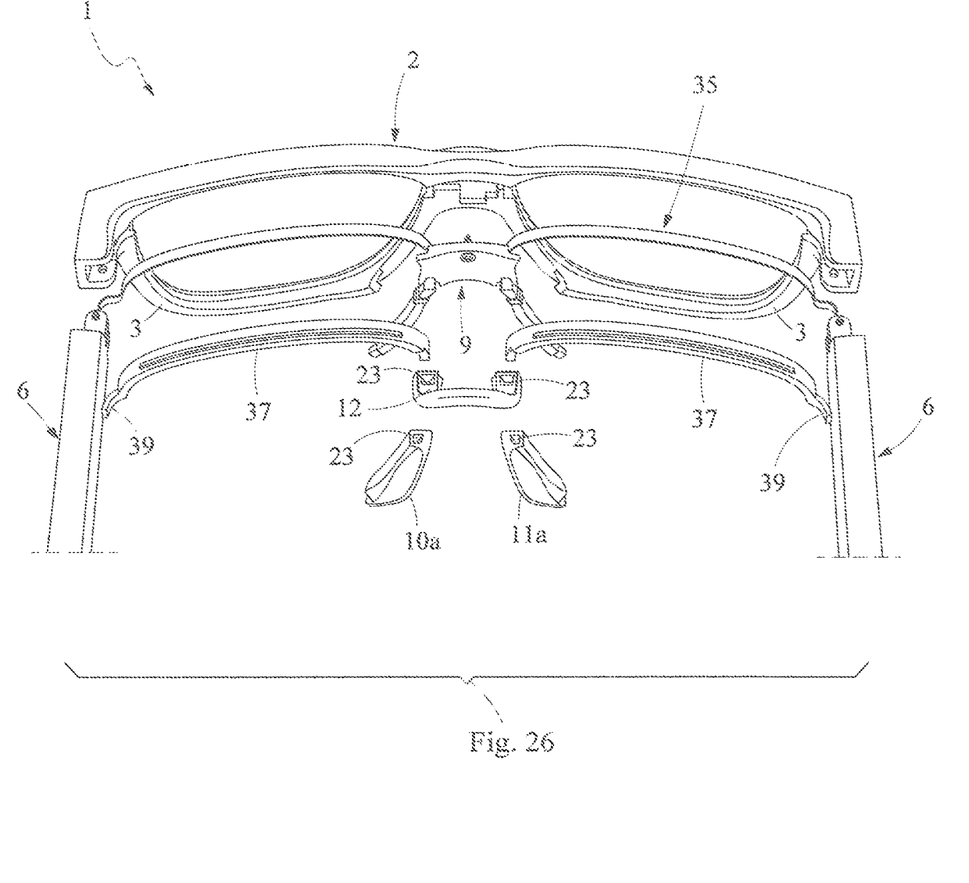
FIG. 26 is a partial perspective view, in which parts of the glasses in the preceding figures have been detached.

FIGS. 19 and 20 schematically show the circuit 35 (shown by a dashed line) housed in the frame between the bridge 5 and the housing 33 of the side, which circuit extends in the passage from the front frame to the lateral side without interruption. FIGS. 22 and 26 are detailed views of the flexible circuit 35 in its overall preferred embodiment, while FIG. 23 shows a partial and schematic illustration of said circuit.

A recess or groove 38 for allowing the passage of the circuit 35 until it is inserted into the housing 33 of the side is also provided in the hinged zone of the side.

Figure 21:
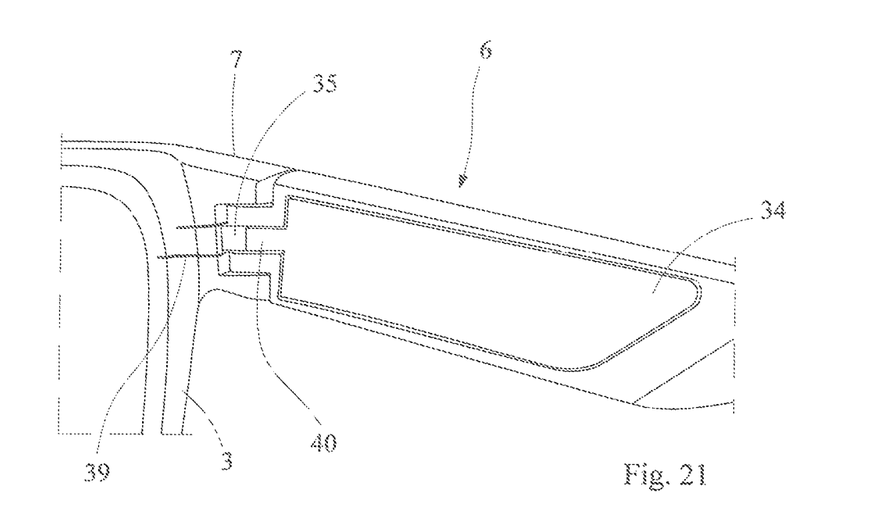
FIG. 21 is a partially perspective and partially assembled enlarged view of the frame detail in FIGS. 19 and 20.

Reference numerals 39 and 40 also designate tabs protruding from the end of the insert 37 and of the cover 34, respectively, which face one another and which, by overlapping the circuit 35, are also used to further conceal said circuit in the hinged zone (FIGS. 21 and 22). As shown in detail in FIG. 21, in this zone, the circuit 35, is in an internal position with respect to the hinge screw in the passage between the end piece and the side, thus being interposed between the hinge screw and the user's face when the glasses are being worn.

In order to establish the electrical contact between the circuit 35 and the sensors 10a, 11a and 12 integrated in the nasal-bearing device 8, respective covers made of conductive material are provided in corresponding positions that are suitable for establishing the electrical contact between the sensor and a respective conductive track of the circuit, while a configuration that also guarantees that the sensors and the corresponding conductive tracks which are in contact with one another are electrically insulated from one another.

FIG. 23 is a schematic view of an embodiment of a Flex PCB circuit 35, comprising a central zone 41, which electrically connects the sensors 10a, 11a and 12 of the nasal-bearing device, from which said sensors extend on opposite sides, two respective conductor lines 42 and 43, line 42 being directed towards the battery for supplying electricity that is housed in one of the lateral sides, and line 43 instead being directed towards the electronic module 32 that is housed in the other lateral side.

The central zone 41 of the circuit is provided to be interposed between the recess 2a in the frame, which recess houses the framework 9, and the framework 9 itself. In order to ensure electrical contact, respective zones covered with electrically conductive material (for example gold), which are indicated by reference numerals 10a', 11a' and 12' and shown schematically by hatching, are provided for direct contact with the sensors 10a, 11a and 12, respectively. Conductive portions, which are only shown in part in FIG. 23, are integrated in the circuit in order to conduct the electrical signals and are appropriately insulated from one another.

By fixing the framework 9 to the frame 2, electrical contact is therefore established between the nasal sensors and the electrical circuit 35 in order to correctly conduct the signals.

Reference numeral 44 designates and only schematically shows the electrical contacts formed at the end of the conductor line 43 of the circuit, which can be electrically connected to the electronic module 32.

In order to make mounting and production easier, the circuit 35, shown in FIG. 23, may preferably be formed in two separate pieces, which, once applied to the front frame, are electrically connected to one another (at the median plane of the front, shown by the central axis indicated in FIG. 23).

Reference sign 50 designates electrical contacts that are provided on the electronic module 32 and are accessible for electrical connection by means of corresponding through-holes 51 made in the cover 34, said contacts forming electrical connections with external electronic devices (for example external power supplies or other additional electronic devices).

Reference numeral 52 designates a connection or centring pin that is in an upright position inside the housing 33 and provided for engaging in a corresponding opening made in the electronic module 32, in order to make it easier to mount the electronic module inside the housing.

The invention meets the objects set, thereby achieving the stated advantages with respect to the known solutions.

One main advantage is that the glasses of the invention make it possible to render the biosensors integrated in the frame more efficient and reliable with regards to the localised electrical contact with the face, thereby ensuring reasonable comfort and fit adaptability with regards to the physical contact between the glasses and the head.

The invention claimed is:

1. Glasses provided with biosensors, for detecting signals, that are in contact with a user's head, the glasses comprising a front frame (2) for supporting respective lenses (4), a pair of sides (6) articulated to the frame on laterally opposing sides and a nasal bearing device (8), each of said sides (6) extending in a longitudinal extension direction and including a side body (6a) that is extended in an end portion (6b) of the side, in which a sensor (25), which can make contact with the user's head, is integrated said side end portion (6b) comprises a pair of arms (26a, 26b) extending, from a common end (27) connected to the side body (6a), in the longitudinal extension direction of the side (6) at a spacing from one another, one (26a) of said arms is provided with an internal cavity (29) for housing a core (30) made of conductive metal material, and in that both said arms (26a, 26b) are made of an resiliently pliable and electrically conductive material, wherein said arms (26a, 26b) are interconnected at the free end of said side end portion (6b) that is opposite the end (27) that is connected to the side body (6a), such that a slotted through-hole (28) remains defined between said arms, said through-hole is elongate in said longitudinal extension direction and has a profile having a closed contour.

2. The glasses according to claim 1, wherein said arms (26a, 26b) are made of an elastomer or rubber.

3. The glasses according to claim 1, wherein the arms (26a, 26b) of said side end portion (6b) are produced by injection molding technology and one (26a) of the two arms is overfolded on said metal core (30).

4. The glasses according to claim 3, wherein each side (6) is produced by over-injecting the side body (6a) on the engagement limb (31) of the metal core (30), and successively over-injecting the side end portion (6b) on the metal core.

5. The glasses according to claim 1, wherein said core (30) can be plastically deformed such that the shape of the side end portion (6b) can be adjusted in order to adapt to the user's head.

6. Glasses provided with biosensors, for detecting signals, that are in contact with a user's head, the glasses comprising a front frame (2) for supporting respective lenses (4), a pair of sides (6) articulated to the frame on laterally opposing sides and a nasal bearing device (8), each of said sides (6) extending in a longitudinal extension direction and including a side body (6a) that is extended in an end portion (6b) of the side, in which a sensor (25), which can make contact with the user's head, is integrated said side end portion (6b) comprises a pair of arms (26a, 26b) extending, from a common end (27) connected to the side body (6a), in the longitudinal extension direction of the side (6) at a spacing from one another, one (26a) of said arms is provided with an internal cavity (29) for housing a core (30) made of conductive metal material, and in that both said arms (26a, 26b) are made of an resiliently pliable and electrically conductive material, wherein said metal core (30) is elongate, at the common end (27) of said arms that is connected to the side body (6a), in a limb (31) that engages in the side body and can be electrically connected to an electronic module (32) housed in the side body or directly electrically connected to a flexible PCB inserted into the side body.

7. The glasses according to claim 6, wherein said side body (6a) comprises a housing (33) that can be closed by a particular removable cover (34), said electronic module (32) that is electrically connected to said core (30) in order to conduct the signals detected by the sensor (25) being received in said housing, said limb (31) projecting into the interior of said housing (33) in order to electrically connect the core (30) to the electronic module.

8. The glasses according to claim 7, wherein a battery (45) for supplying electrical energy is received in said housing together with said electronic module, battery and electronic module are electrically interconnected.

9. The glasses according to claim 6, wherein said side body (6a) comprises a housing (33) that can be closed by a particular removable cover (34), said electronic module (32) and a battery for supplying electrical energy to said electronic module being received in said housing.

* * * * *